United States Patent [19]

Smith

[11] Patent Number: 5,725,565
[45] Date of Patent: Mar. 10, 1998

[54] TANNING BED SAFETY DEVICE

[76] Inventor: Daniel E. Smith, 421 Santa Fe Ave., Branson, Mo. 65616

[21] Appl. No.: 567,523

[22] Filed: Dec. 4, 1995

[51] Int. Cl.⁶ .................................................. A61N 5/06
[52] U.S. Cl. ............................ 607/88; 607/94; 368/108; 368/10
[58] Field of Search ........................ 607/88–94, 96; 315/97, 324, 360; 368/10, 108; 250/372, 494.1, 493.1, 504 R

[56] References Cited

U.S. PATENT DOCUMENTS

| | | |
|---|---|---|
| 4,013,922 | 3/1977 | Van Der Meulen . |
| 4,095,139 | 6/1978 | Symonds et al. . |
| 4,279,254 | 7/1981 | Boschetti et al. . |
| 4,283,661 | 8/1981 | Doty . |
| 4,312,436 | 1/1982 | Martin et al. . |
| 4,428,050 | 1/1984 | Pellegrino et al. . |
| 4,683,888 | 8/1987 | Kramer et al. .............. 607/91 |
| 4,726,377 | 2/1988 | Jegers et al. . |
| 4,729,375 | 3/1988 | Jegers et al. . |
| 4,835,749 | 5/1989 | Welton . |
| 4,888,525 | 12/1989 | Nilssen . |
| 4,888,526 | 12/1989 | Nilssen . |
| 4,893,064 | 1/1990 | Nilssen . |
| 4,896,078 | 1/1990 | Nilssen . |
| 4,980,900 | 12/1990 | Welton . |
| 5,021,717 | 6/1991 | Nilssen . |
| 5,086,770 | 2/1992 | Prangley .................. 607/88 |
| 5,363,347 | 11/1994 | Nguyen .................. 607/88 X |
| 5,374,825 | 12/1994 | Doty et al. . |

*Primary Examiner*—Jennifer Bahr
*Assistant Examiner*—Ryan Carter
*Attorney, Agent, or Firm*—Hovey, Williams, Timmons & Collins

[57] ABSTRACT

A tanning bed control system including a tanning bed safety device (10) for ensuring safe operation of a tanning bed (14) is disclosed. The tanning bed safety device (10) monitors the operation of the tanning bed (14) and the tanning bed controller (12) and activates an alarm if the tanning bed (14) is on when it should be off or off when it should be on.

3 Claims, 2 Drawing Sheets

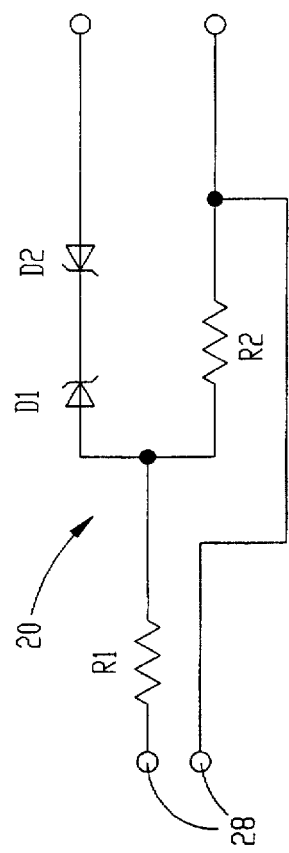
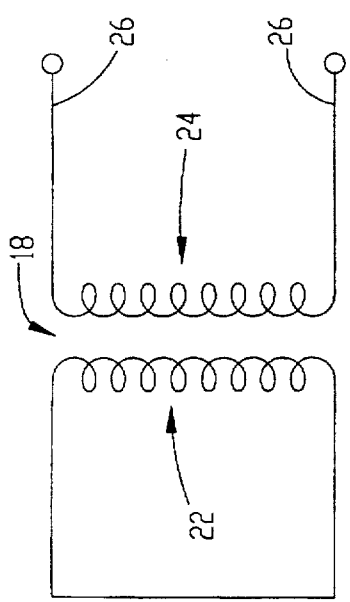
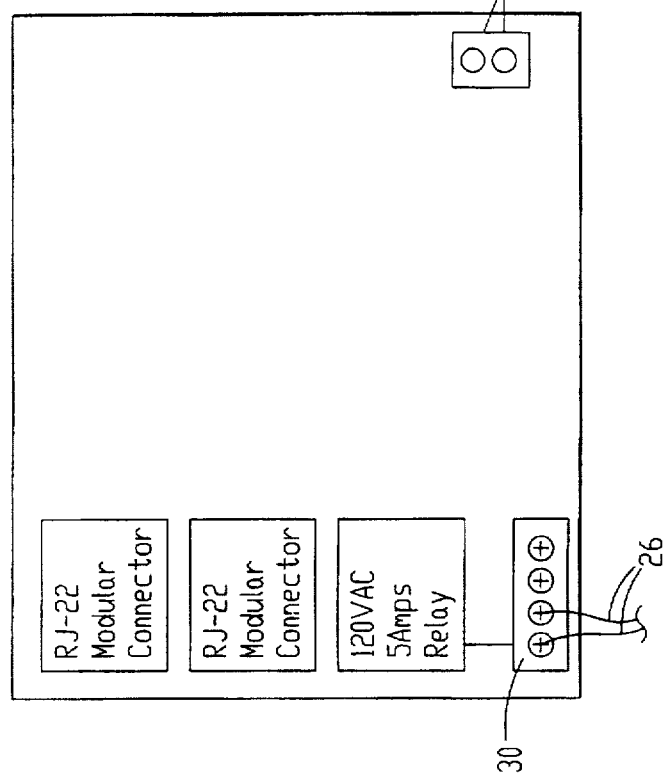

TANNING BED SAFETY DEVICE

BACKGROUND OF THE INVENTION

1. Field of the Invention

The present invention relates to tanning bed control systems, and more particularly to a tanning bed safety device for use with a tanning bed controller for ensuring safe operation of a tanning bed. The tanning bed safety device monitors the operation of both the tanning bed and the tanning bed controller and activates an alarm if the tanning bed is operating when it should be off or is off when it should be operating.

2. Description of the Prior Art

Tanning bed controllers for controlling the operation of one or more tanning beds are known in the art. These tanning bed controllers typically include a timer for receiving a desired tanning time and a relay switch responsive to the timer for interrupting the delivery of control power to the tanning bed once the timer has counted down the timer input time. Many tanning bed control systems include a separate controller for each tanning bed. A group of controllers can be positioned at a central operating station so that an operator can control a plurality of tanning beds. A separate controller may also be placed adjacent each controlled tanning bed for allowing the tanning patron to turn the tanning bed on and off.

Although tanning bed controllers provide for effective control of a plurality of tanning beds from a central station, they can cause serious injury to patrons when they malfunction. For example, the relay switches on the controllers, the electrical contactors in the tanning beds, and other control circuitry in the tanning beds sometimes fail due to electrical shorts or other electrical or mechanical failures. When this happens, the contacts and switches in the controllers and/or tanning beds often become inoperative. Thus, the timers in the controllers may read that the tanning beds are off even when power is still being delivered to the tanning beds or read on when no power is being delivered to the tanning beds.

The above-described electrical or mechanical failures can result in serious injury to a tanning patron if the patron continues to be exposed to ultraviolet (UV) tanning rays after the desired tanning time has expired. Since the attendant is often unaware of the error because the controller timer reads that the tanning bed is off, the error may not be discovered until after the tanning patron has been seriously burned.

OBJECTS AND SUMMARY OF THE INVENTION

In view of the above-described limitations in prior art tanning bed control systems, it is an object of the present invention to provide a tanning bed safety device that ensures safe operation of one or more tanning beds.

It is a more particular object of the present invention to provide a tanning bed safety device that alerts an attendant when a tanning bed controller or tanning bed is malfunctioning.

It is another object of the present invention to provide a tanning bed safety device that monitors the operation of both the tanning bed and the controller and alerts the attendant either when the tanning bed is on when it should be off or off when it should be on.

In view of these and other objects that become evident from the following description of the invention, a tanning bed safety device for use with a tanning bed controller for controlling the operation of a tanning bed is provided.

In more detail, the tanning bed safety device is preferably used with a tanning bed controller including a timer and a relay switch. The timer is operable for receiving a timer input representative of a desired tanning time and for counting down the timer input time. The relay switch is responsive to the timer and is provided for switching control power to the tanning bed while the timer is counting down the timer input time and for interrupting the delivery of control power to the tanning bed when the timer has counted down the timer input time.

The tanning bed safety device ensures proper and safe operation of both the tanning bed controller and the tanning bed controlled by the tanning bed controller. The tanning bed safety device broadly includes a sensing means for sensing or monitoring the operation of the tanning bed, monitoring means for monitoring the status of the tanning bed controller timer, and an alarm activating means responsive to the sensing means and the monitoring means for activating an alarm when the tanning bed is in operation after the timer has counted down the timer input time.

In preferred forms, the sensing means includes a current sensing transformer and a diode voltage clipping circuit. The primary winding of the current sensing transformer is coupled with a current-carrying conductor of the tanning bed for sensing the flow of current through the current-carrying conductor. The diode voltage clipping circuit is coupled with the secondary winding of the current sensing transformer and provides an output signal to the tanning bed controller only if current greater than or equal to a pre-determined amount is sensed by the current sensing transformer. In this way, the sensing means only produces an output signal when the tanning bed is drawing a sufficient amount of current to operate the tanning bulbs. This allows the operation of the tanning bed's cooling fans without providing an output signal that indicates that the tanning bed is on.

The monitoring means is preferably software residing in the tanning bed controller that monitors the status of the tanning bed controller timer.

The alarm activating means is responsive to the sensing means and the monitoring means for activating an alarm when the tanning bed controller or tanning bed malfunctions. The alarm activating means compares the condition of the tanning bed controller's timer with the condition of the sensing means and triggers the alarm when the tanning bed is on when it should be off or off when it should be on. The alarm may be provided either in the controller or remote from the controller.

The tanning bed safety device may be provided as a separate circuit that provides an input to the tanning bed controller or may be formed as an integral component of a tanning bed controller.

By constructing a tanning bed safety device as disclosed herein, numerous advantages are realized. For example, by constructing a tanning bed safety device that monitors both the operation of a tanning bed and the tanning bed controller and alerts an attendant when either is malfunctioning, injuries resulting from over exposure to UV tanning rays due to faulty control equipment can be eliminated.

More particularly, by constructing a tanning bed safety device that senses the operation of a tanning bed, monitors the status of the timer of the tanning bed controller, and alerts the attendant either when the tanning bed is on when it should be off or off when it should be on, the invention provides a secondary safety feature that is independent of the tanning bed controller for ensuring proper operation of a tanning bed. Thus, the tanning bed safety device prevents injuries due to over exposure to UV tanning rays even when the tanning bed controller malfunctions.

BRIEF DESCRIPTION OF THE DRAWING FIGURES

A preferred embodiment of the present invention is described in detail below with reference to the attached drawing figures, wherein:

FIG. 2 is a schematic diagram of a first component of the sensing means of the tanning bed safety device;

FIG. 3 is a schematic diagram of a second component of the sensing means of the tanning bed safety device; and FIG. 4 is a block diagram illustrating the rear of a tanning bed controller used with the tanning bed safety device of the present invention.

DETAILED DESCRIPTION OF THE PREFERRED EMBODIMENTS

Figure 1:
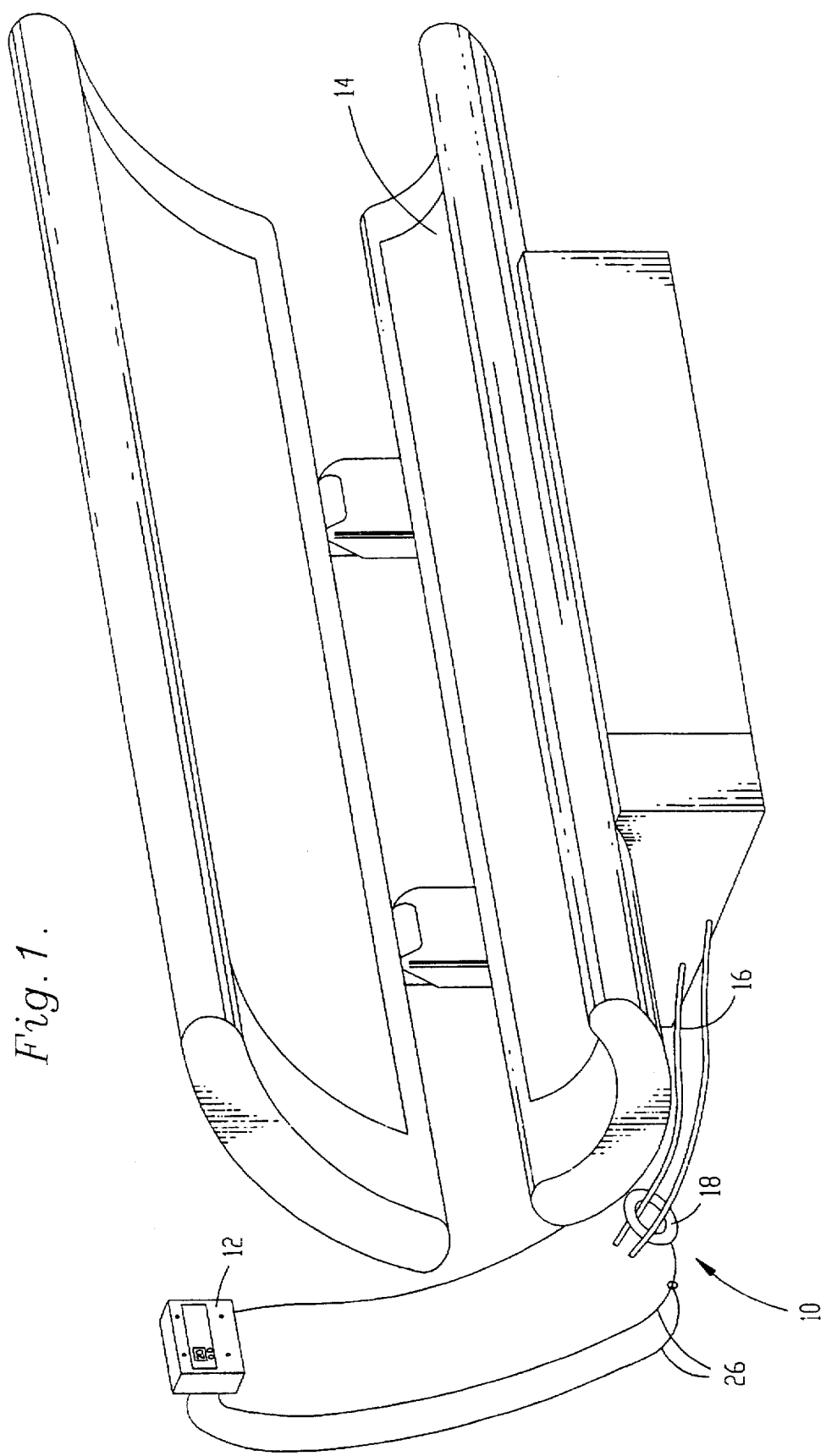
FIG. 1 is a perspective view of the tanning bed safety device of the present invention shown coupled with a tanning bed controller and a tanning bed.

Turning now to FIG. 1, a tanning bed safety device broadly referred to by the numeral 10 and constructed in accordance with a preferred embodiment of the present invention is shown coupled with a tanning bed controller 12 and a tanning bed 14. The tanning bed safety device 10 monitors the operation of both the tanning bed 14 and the tanning bed controller 12 and provides a secondary safety feature that ensures the safe operation of the tanning bed 14.

In more detail, the tanning bed controller 12 is operable for controlling the operation of a tanning bed 14. The tanning bed controller 12 may be positioned at a central control station or adjacent the tanning bed 14. A separate controller may also be positioned at both locations. Examples of tanning bed controllers of the type with which the tanning bed safety device 10 of the present invention may be used are the T-Max Series Timers and Controllers manufactured by Salon Systems, Inc.

The tanning bed controller 12 includes a timer and a relay switch. The timer is operable for receiving a timer input representative of a desired tanning time and for counting down the timer input time. The relay switch is responsive to the timer and is provided for switching control power to the tanning bed 14. The relay switch switches control power to the tanning bed 14 after the timer is started and interrupts the delivery of control power to the tanning bed 14 when the timer has counted down the timer input time.

The tanning bed 14 is conventional and is connected to a source of electricity by a current-carrying conductor 16. An example of a tanning bed 14 of the type with which the tanning bed controller 12 and safety device 10 may be used is the Wolfe brand tanning beds.

The tanning bed safety device 10 monitors the operation of both the tanning bed 14 and the tanning bed controller 12 and provides a secondary safety feature that operates in conjunction with the tanning bed controller timer and relay switch for ensuring the safe operation of the tanning bed 14. The tanning bed safety device 10 may be provided as a separate circuit that provides an input to the tanning bed controller 12 or may be formed as an integral component of a tanning bed controller 12.

The preferred tanning bed safety device 10 broadly includes a sensing means depicted in FIGS. 2 and 3 for sensing or monitoring the operation of the tanning bed 14, monitoring means for monitoring the operation of the tanning bed controller 12, and an alarm activating means responsive to the sensing means and the monitoring means for activating an alarm when either the tanning bed controller 12 or tanning bed 14 is malfunctioning.

In more detail, the sensing means senses or monitors the operation of the tanning bed 14 and creates and transmits an output signal to the alarm activating means when the tanning bed 14 is on. As illustrated in FIGS. 2 and 3, the sensing means preferably includes a current sensing transformer 18 and a diode voltage clipping circuit 20.

The current-sensing transformer 18 senses when current is delivered to the tanning bed 14 for monitoring the operation of the tanning bed 14. The current sensing transformer 18 is conventional in construction and may be provided by any electronics manufacturer.

The current-sensing transformer 18 includes a primary winding 22 and a secondary winding 24 as depicted in FIG. 2. As illustrated in FIG. 1, the current sensing transformer 18 is preferably in the form of a loop having a pair of electrical leads 26 extending therefrom. A current-carrying conductor 16 of the tanning bed 14 is threaded through the loop so that the current-sensing transformer 18 circumscribes the conductor 16.

When power is delivered to the tanning bed 14 through the current-carrying conductor 16, the primary winding 22 senses the current in accordance with well-known principles of electromagnetism. The secondary winding 24 then steps down or reduces the sensed current to a lower control level and delivers the current to the diode voltage clipping circuit 20 as described below. In preferred forms, the windings of the current sensing transformer 18 provide a 5,000:1 step-down ratio.

The output terminals or leads 26 of the secondary winding 24 of the current-sensing transformer 18 are coupled with the input terminals 28 of the diode voltage clipping circuit 20. As described in more detail below, the diode voltage clipping circuit 20 is preferably formed on the tanning bed controller 12. Thus, as illustrated in FIG. 4, the electrical leads 26 of the current-sensing transformer 18 are connected to a input terminal block 30 on the back of the tanning bed controller 12 for delivering the sensed current to the diode voltage clipping circuit 20.

The diode voltage clipping circuit 20 is provided for clipping the current signal sensed by the current-sensing transformer 18 and includes a pair of Zener diodes D1 and D2 and a pair of resistors R1 and R2. The diodes D1 and D2 and resistors R1 and R2 are configured for receiving the sensed current from the secondary winding 24 of the current-sensing transformer 18 and for producing an output signal only when the current sensed by the current-sensing transformer 18 is in excess of a pre-determined amount. This output signal is used as a first input to the alarm activating means as described below.

In preferred forms, the diode voltage clipping circuit 20 produces an output signal when current greater than or equal to 10 amps passes through the primary winding 22 of the current-sensing transformer 18. In this way, the sensing means only delivers an output signal to the tanning bed controller 12 when the tanning bed 14 is drawing a sufficient amount of current to operate the tanning bulbs, thus allowing the operation of the tanning bed's cooling fans without providing an output signal that indicates that the tanning bed 14 is on.

As described above, the diode voltage clipping circuit 20 is preferably wired on a circuit board of the tanning bed controller 12. The diode voltage clipping circuit 20 may also be provided as a stand-alone circuit or may be wired directly with the current-sensing transformer 18.

The monitoring means monitors the status of the tanning bed controller timer and provides a second input to the alarm activating means. The function of the monitoring means is preferably performed by software residing in the tanning bed controller 12. The source code for this portion of the software is reproduced in the attached Software Appendix.

The alarm activating means monitors the output signals from the diode voltage clipping circuit 20 and the monitoring means and determines whether the tanning bed controller 12 and tanning bed 14 are operating properly. When the alarm activating means determines that the tanning bed controller 12 or the tanning bed 14 is malfunctioning, it activates an alarm.

More particularly, the alarm activating means compares the status of the tanning bed controller's timer with the output signal generated by the diode voltage clipping circuit 20 and triggers an alarm when the tanning bed 14 is on when it should be off, or off when it should be on. For example, if the diode voltage clipping circuit 20 generates an output signal indicating that the tanning bed 14 is in operation after the tanning bed controller timer has counted down the timer input time, the alarm activating means determines that the tanning bed 14 is on when it should be off. Thus, the alarm activating means activates an alarm. Similarly, if the diode voltage clipping circuit 20 does not generate an output signal while the timer is operating, the alarm activating means determines that the tanning bed 14 is off when it should be on.

The function of the alarm activating means is preferably performed by software that resides in the memory of the tanning bed controller. The software program monitors both the status of the tanning bed controller timer and the output signal generated by the diode voltage clipping circuit 20 and determines whether the tanning bed controller 12 is malfunctioning as described above. If the alarm activating means determines that the tanning bed controller 12 is malfunctioning, it triggers an alarm. The source code for this portion of the software is reproduced in the attached Software Appendix. Those skilled in the art will appreciate that the alarm activating means may also be provided as an electronic circuit hard-wired to the tanning bed controller circuit board or the sensing means.

The alarm that is activated by the alarm activating means is preferably an audible alarm. The alarm may be integrally provided with the tanning bed controller 12 or may be a separate alarm that is electrically connected with the tanning bed controller 12 and positioned remotely from the controller 12.

Although the invention has been described with reference to the preferred embodiment illustrated in the attached drawing figures, it is noted that equivalents may be employed and substitutions made herein without departing from the scope of the invention as recited in the claims. For example, the current transformer and diode voltage clipping circuit of the sensing means may be replaced with other types of sensing and detecting devices for sensing or monitoring the operation of the tanning bed. Particularly, the sensing means may include a photodiode or similar type photosensitive semiconductor device for sensing the operation of the tanning bed tanning bulbs and for providing and output signal when the tanning bed bulbs are in operation. Similarly, the sensing means may include a heat sensor for sensing the temperature of the tanning bed tanning bulbs and for providing an output signal when the temperature of the tanning bulbs has risen to a level indicating that they are in operation.

SOURCE CODE APPENDIX

An appendix containing the source code of a computer program used with the present invention is appended hereto.

| SOURCE CODE APPENDIX | | |
|---|---|---|
| CurCk | btfsc | Sense |
| | goto | CC |
| | movlw | 50 |
| | movwf | CurTime |
| | bsf | CurOn |
| CC | btfsc | CurErrDelay |
| | return | |
| | movlw | ParmCurSense |
| | call | GetParmL |
| | btfsc | _z |
| | return | |
| | btfss | LampRelay |
| | goto | CCOff |
| | btfsc | CurOn |
| | return | |
| | movlw | CurErrorOff |
| CCErr | movwf | ErrorCode |
| | bsf | Help |
| | return | |
| CCOff | btfss | CurOn |
| | return | |
| | movlw | CurErrorOn |
| | goto | CCErr |
| LampOn | bsf | LampRelay |
| | movlw | 100 |
| | goto | LO |
| LampOff | bcf | LampRelay |
| | movlw | 100 |
| LO | movwf | CurErrTime |
| | bsf | CurErrDelay |
| | return | |
| | decf | CurTime, f |
| | btfsc | _z |
| | bcf | CurOn |
| | decf | CurErrTime, f |
| | btfsc | _z |
| | bcf | CurErrDelay |

Having thus described the preferred embodiment of the invention, what is claimed as new and desired to be protected by Letters Patent includes the following:

1. A tanning bed safety device for use with a tanning bed controller coupled with a tanning bed having a plurality of tanning bed bulbs, the tanning bed controller including a timer and a switch means responsive to the timer for controlling operation of the tanning bed, said tanning bed safety device comprising:

sensing means for sensing the operation of the tanning bed independently of the operation of the tanning bed controller;

monitoring means for monitoring the operation of the timer; and alarm activating means responsive to said sensing means and said monitoring means for activating an alarm signal if the tanning bed remains in operation after the timer has stopped operating, said sensing means including a heat sensor for sensing the temperature of the tanning bed bulbs for sensing the operation of the tanning bed.

2. A tanning bed safety device for use with a tanning bed controller coupled with a tanning bed having a current-carrying conductor, the tanning bed controller including a timer and a switch means responsive to the timer for controlling operation of the tanning bed, said tanning bed safety device comprising:

sensing means for sensing the operation of the tanning bed independently of the operation of the tanning bed controller;

monitoring means for monitoring the operation of the timer;

alarm activating means responsive to said sensing means and said monitoring means for activating an alarm signal if the tanning bed remains in operation after the timer has stopped operating, said sensing means including a current transformer coupled with the current-carrying conductor of the tanning bed for sensing the flow of current in the conductor for sensing the operation of the tanning bed; and clipping means electrically coupled with said current transformer for delivering an output signal to said alarm activating means when said current transformer senses current in the conductor that exceeds a predetermined level.

3. The tanning bed control system as set forth in claim 2, said clipping means including a diode voltage clipping circuit having a pair of zener diodes and a pair of resistors.

* * * * *